United States Patent [19]
Gourlandt
[11] 4,375,814
[45] Mar. 8, 1983

[54] METHOD AND APPARATUS FOR AUTOMATICALLY SUPPORTING AND RESTRAINING BIRDS, AND PREFERABLY YOUNG CHICKS, SAID METHOD AND APPARATUS IN A PREFERRED EMBODIMENT BEING APPLIED FOR AUTOMATICALLY DEBEAKING SAID BIRDS

[76] Inventor: Albert J. A. Gourlandt, Les Gresillons, 78950 Gambais, France

[21] Appl. No.: 184,970

[22] Filed: Sep. 8, 1980

[30] Foreign Application Priority Data

Sep. 14, 1979 [FR] France ................................ 79 23018

[51] Int. Cl.³ ........................ A61B 17/00; A61D 1/00; A01K 37/00

[52] U.S. Cl. .................................. 128/253; 119/97 R

[58] Field of Search ........................ 128/253, 223, 222; 119/97 R, 97; 17/44.1

[56] References Cited

U.S. PATENT DOCUMENTS 2,448,421 8/1948 Davis .................................. 17/44.1
2,731,016 1/1956 Miller .................................. 128/253
2,952,031 9/1960 Breitkreutz .................. 119/97 R X
3,302,645 2/1967 Lockmiller .......................... 128/223
3,774,578 11/1973 Randolph et al. ................ 119/97 R

*Primary Examiner*—Hugh R. Chamblee

[57] ABSTRACT

The invention relates to a method and apparatus for automatically restraining notably birds, applicable preferably for debeaking birds.

The apparatus comprises a turntable 20 rotatively mounted onto a frame 1, the table 20 comprising a plurality of bird supports 30 spaced apart on said table 20, each support 30 comprising means 32 for suspending a bird by its head, preferably a debeaking assembly 34 in the vicinity of said table 20; drive means 27 for moving said table 20; preferably actuator means 41 for actuating said debeaking assembly 34 to its operative position upon arrival of a support 30 at the debeaking station 35 and thereafter returning the assembly 34 to its non-operative position, and release means 98 to release the bird from its support 30 upon arrival at the unloading station 40.

The invention allows to debeak up to 6000 birds per hour.

36 Claims, 18 Drawing Figures

METHOD AND APPARATUS FOR AUTOMATICALLY SUPPORTING AND RESTRAINING BIRDS, AND PREFERABLY YOUNG CHICKS, SAID METHOD AND APPARATUS IN A PREFERRED EMBODIMENT BEING APPLIED FOR AUTOMATICALLY DEBEAKING SAID BIRDS

The invention essentially relates to a method and an apparatus for automatically supporting and restraining notably birds, and preferably young chicks, said method and apparatus being in a preferred embodiment applied for debeaking birds.

The practice of cutting and cauterizing birds' beaks to minimize cannibalism is wide spread in the chicken raising industry.

According to the present invention, is provided an improved method and apparatus for automatically supporting and restraining notably birds, said method and apparatus being preferably applied for automatically debeaking birds.

The method according to the invention generally comprises:

providing a table rotatively mounted onto a frame, said table comprising a plurality of bird supports spaced apart on said table, each bird support comprising means for suspending a bird by its head with the head immobilized, moving said table in rotation so that each support successively passes in a bird loading station and in a bird unloading station, inserting a bird into each support in said bird loading station, and releasing said bird from the support in said bird unloading station.

In a preferred embodiment of the invention method, for automatically debeaking birds, said method further comprises:

disposing a debeaking assembly in the vicinity of said table downstream with respect to said loading station but upstream with respect to said unloading station, said debeaking assembly comprising a debeaking element, movable between an operative position and a non-operative position, so that each support passes in the debeaking assembly station, and moving the debeaking assembly to its operative position upon arrival of a support at said debeaking assembly station and thereafter returning said debeaking assembly to its nonoperative position after a predetermined period of time sufficient to realize the debeaking operation.

Advantageously, this method further comprises:

moving continuously in rotation the table, at a predetermined substantially constant speed, moving in rotation the debeaking assembly, at the same rotation speed as the table, during the period of time where the debeaking assembly with its debeaking element is in its operative position so that the debeaking assembly follows in rotation the support with the brid in the debeaking operation thereby providing a proper debeaking, moving the debeaking assembly in rotation in a contrary direction with respect to the table rotation direction when the debeaking assembly is returned in its non-operative position so as to return the debeaking assembly in its original position before debeaking.

According to a specific embodiment, this method also comprises lowering the debeaking assembly from its non-operative position located above the table at the same time the debeaking assembly is rotated to follow the table rotation; and rotating horizontally with respect to the debeaking assembly the debeaking element towards the facing support so as to debeak the facing bird. According to this specific embodiment, the upper and lower beaks of the bird are debeaked.

According to another embodiment of the method, said method comprises lowering the debeaking assembly from its non-operative position located above the table at the same time the debeaking assembly is rotated to follow the table rotation; and only vertically lowering with the debeaking assembly the debeaking element so as to debeak only the upper beak of the bird.

This invention also relates to an apparatus for automatically supporting and restraining notably birds, essentially comprising:

a table rotatively mounted onto a frame, said table comprising a plurality of bird supports spaced apart on said table, each bird support comprising means for suspending a bird by its head with the head immobilized, drive means for moving said table to cause each support to pass first to a loading station and thereafter to an unloading station, and release means for causing a support to release its bird upon arrival at said unloading station.

In a preferred embodiment, said invention apparatus further comprises a debeaking assembly at the vicinity of said table downstream with respect to the loading station but upstream with respect to the unloading station, said debeaking assembly comprising a debeaking element, movable between an operative position and a non-operative position so that each support is able to pass, upon rotation of the table, in the debeaking assembly station, and actuator means for actuating said debeaking assembly with its debeaking element to its operative position upon arrival of a support at the debeaking station and thereafter returning the debeaking assembly with its debeaking element to its non-operative position.

Preferred embodiments include the following features, among others: said suspending means of the bird support comprises a front piece constituting at least a part of a headpiece, fixed at said table and having a recess receiving at least a part of a bird's head, said front piece having an opening at the apex of the recess through which the beak protrudes while being held closed. Said suspending means further comprises a pair of shaped retainers mounted on said table for holding a bird's head in said recess. Advantageously, said retainers are arranged to extend across opposite sides of the bird's neck and then up along the head to hold the head in a recess which is preferably conical.

According to another embodiment, the release means comprises a release element for automatically forcing said suspending means to release a bird upon arrival of said support at said unloading station. Advantageously, said suspending means comprises a spring for biasing said retainers in a closed position against a bird and said release means comprises a cam for forcing said retainers apart to an open position to release said bird. Preferably, each said support further comprises a control member in the path of a bird being loaded into said support for actuation of said cam with the aid of a linkage so as to allow said spring to close the retainers upon a bird when the bird is pressed against the control member.

According to a preferred embodiment, said release element is arranged in the path of said linkage to return said cam to its position holding said retainers apart.

The control member also serves as a tongue depressor, by action either against the neck or between the beaks.

The debeaking assembly preferably comprises means to heat said debeaking element to burn the beak tip and said actuator means comprises advantageously means for holding said heated debeaking element against the beak tip with sufficient pressure to char said beak without damaging it so as to avoid to wound or injure said beak thereby allowing the bird to feed itself. The shape of the debeaking element and its movement, are selected to operate either one or both beaks and to produce the desired form and degree of debeaking. The means for heating the debeaking element preferably comprises a gas nozzle and a source of flammable gas and, advantageously a means for providing an air stream into a tube disposed opposite to the gas nozzle to draw off both the hot air (to prevent overheating of any parts that touch the bird) and the smell and smoke around the debeaking element, said air stream being blown into said tube at a location sufficiently spaced from said debeaking element so as to avoid to cool the debeaking element.

The invention thus provides accurately controlled debeaking at a very high speed, requiring only a single operator who quickly and easily loads the birds, such as young chicks. Because the beak is merely burned and is not mechanically damaged upon application of the debeaking element, the beak can be used by the young chick for feeding itself.

Other characterizing features, purposes or advantages of the present invention will appear as the following non-limitative description proceeds with reference to the appended drawings representing the, at the present time, preferred embodiment of the invention apparatus which accordingly as above said allows to automatically debeak birds, wherein.

Figure 1:
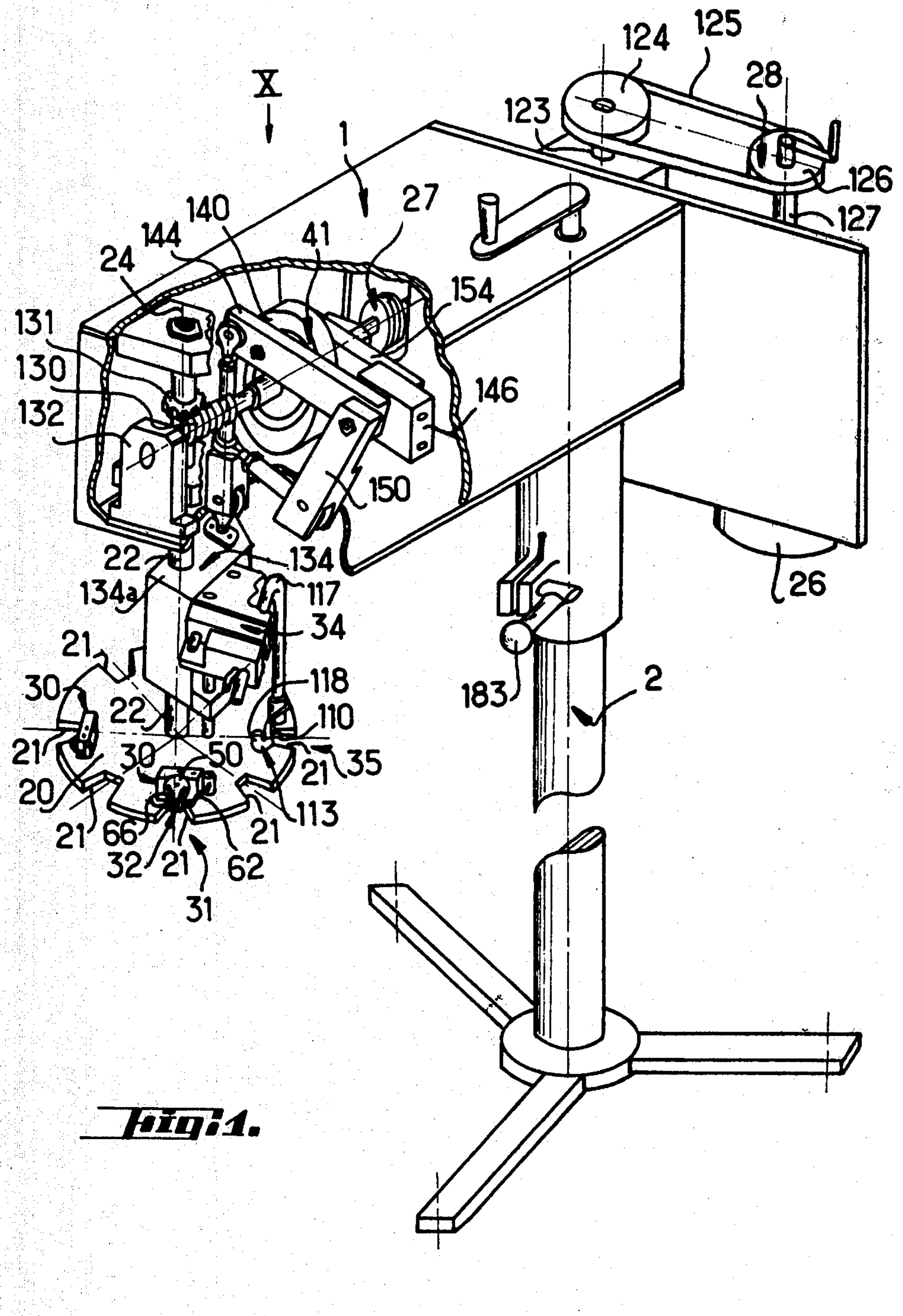
FIG. 1 is a perspective view with some parts of the frame broken away to show more precisely the drive means for moving the rotative table and in the preferred embodiment the actuator means for actuating the debeaking assembly.
Figure 9:
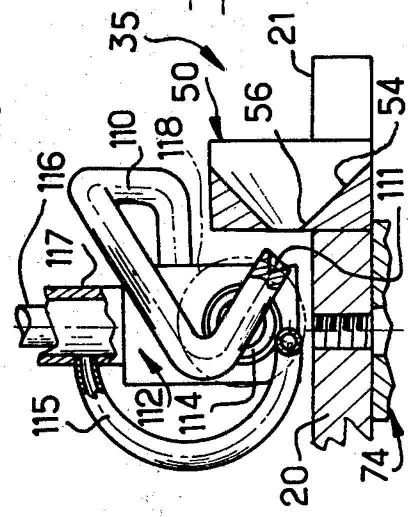
Figure 16:
Figure 17:
Figure 7:
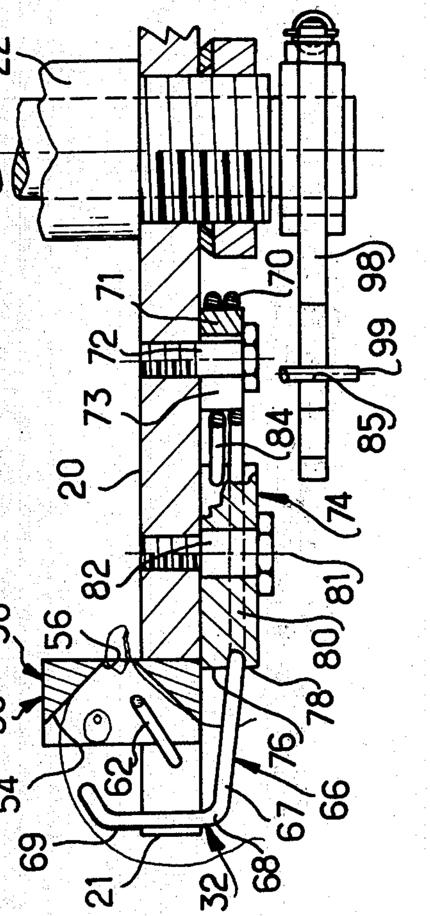
Figure 6A:
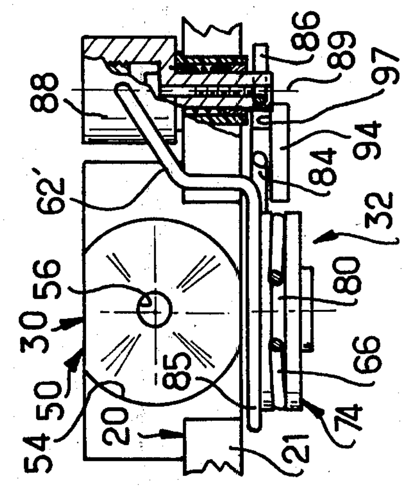
Figure 6:
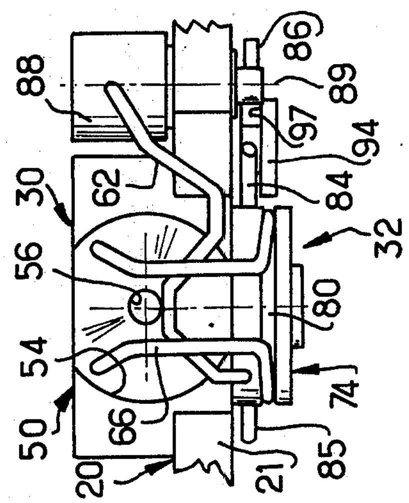
Figure 10:
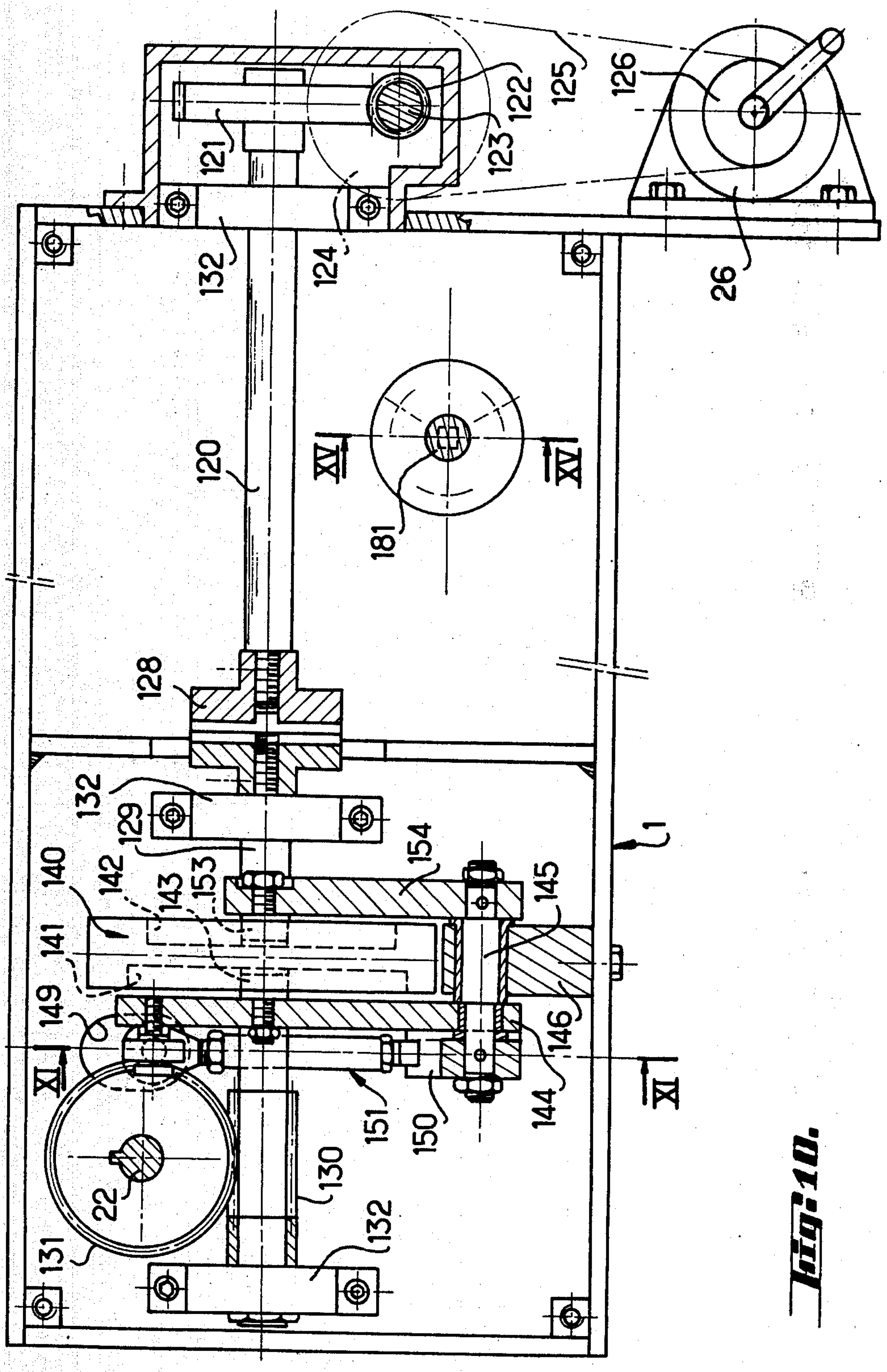
Figure 11:
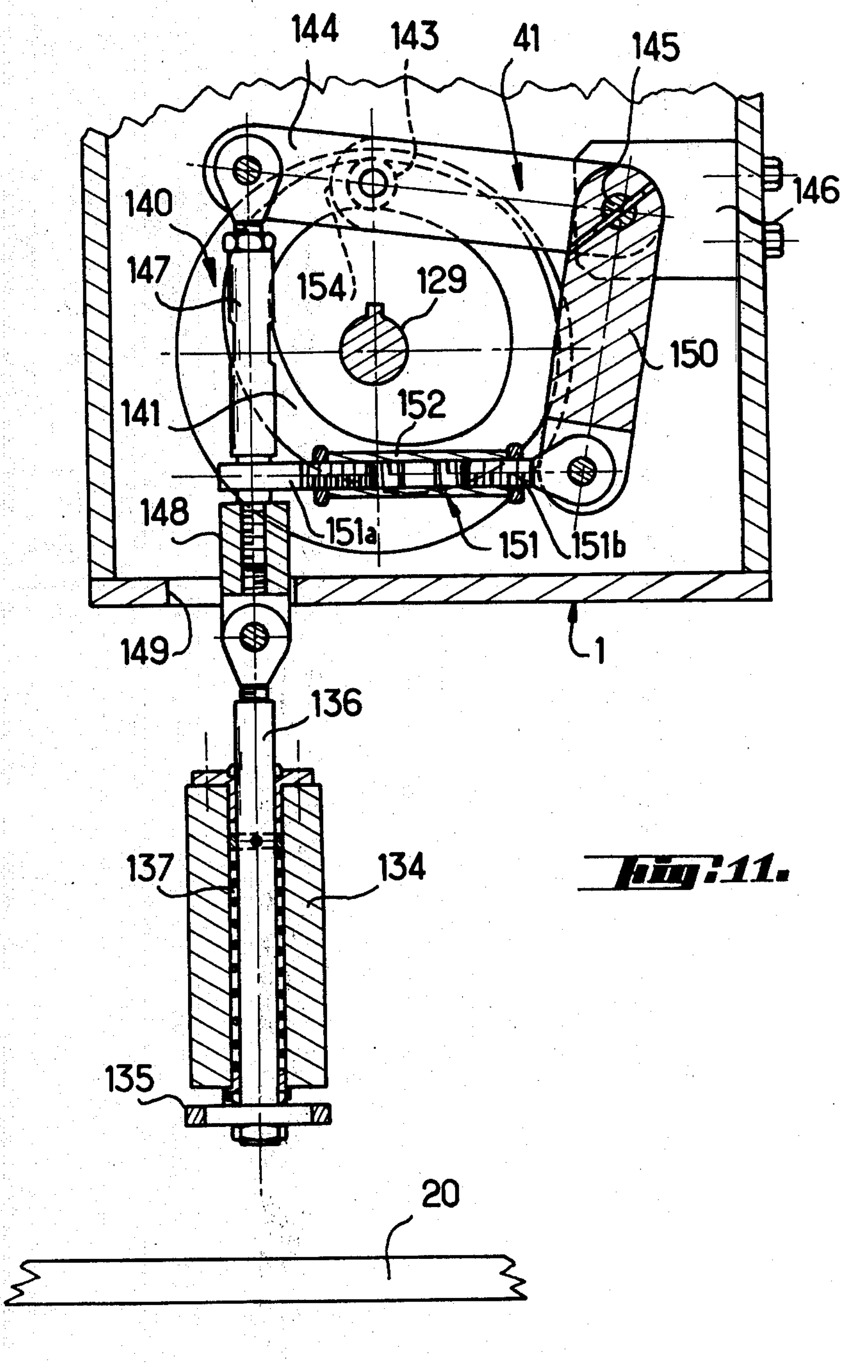
Figure 15:
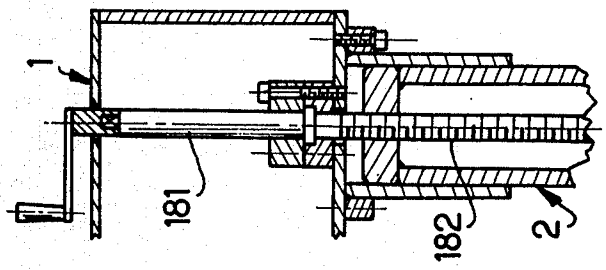
Figure 13:
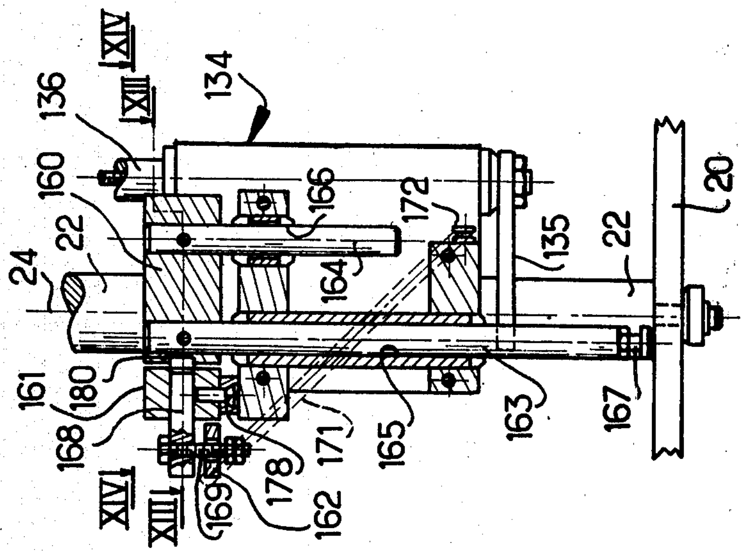
Figure 12:
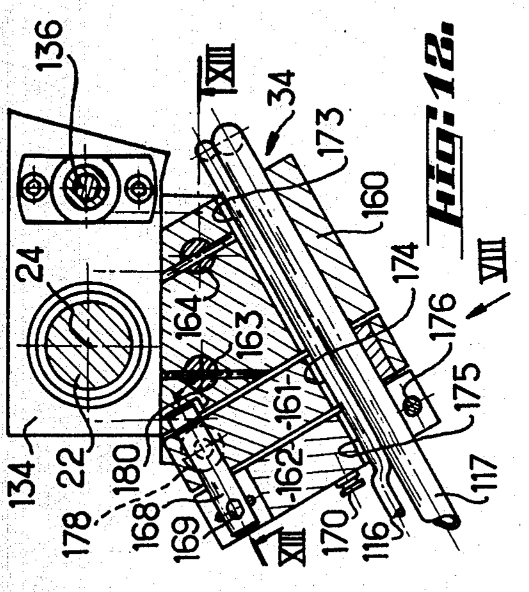
Figure 14:
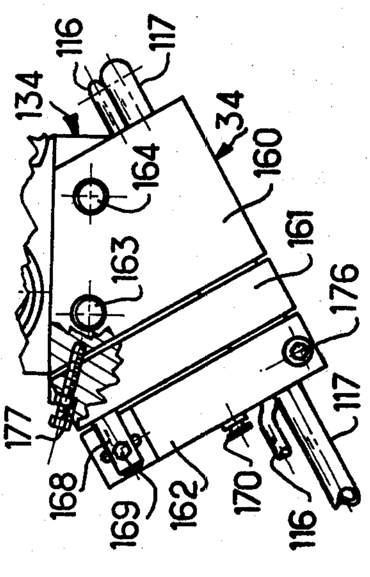

FIG. 6*a* represents a modification of the embodiment shown in FIG. 6 with some parts broken away;

FIG. 7 is a partial cross-section view of the rotative table showing a bird supported by a support;

FIG. 8 shows in perspective more specifically the arrangement of the debeaking assembly according to arrow VIII of FIG. 12;

FIG. 9 shows a detail of the debeaking assembly in operative position on the beak of a bird;

FIG. 10 shows a top view of the apparatus frame according to arrow X of FIG. 1;

FIG. 11 represents the actuator means according to line XI—XI of FIG. 10;

FIG. 12 represents the top of the debeaking assembly with some parts broken away;

FIG. 13 represents a view in longitudinal cross-section according to line XIII—XIII of FIG. 12;

FIG. 14 represents a view analogous to that of FIG. 12 with a partial cross-section showing a means allowing to modify the movement of the debeaking element to modify the debeaking form;

FIG. 15 is a partial cross-section view according to line XV—XV of FIG. 10. FIGS. 16 and 17 represent two embodiments of debeaking element.

Referring to FIG. 1, the invention apparatus comprises a frame 1 mounted displaceable onto a support base 2 bearing on the ground. The apparatus comprises a table 20 rotatively mounted onto the frame 1, supported by spindle 22 for rotation about axis 24 by motor 26 through a drive means 27 including variable speed drive transmission 28.

Turntable 20 has eight notches 21 at which are mounted bird supports 30 for receiving birds at loading station 31. Each bird support 30 comprises means 32 for suspending a bird by its head with the head immobilized.

Figure 2:
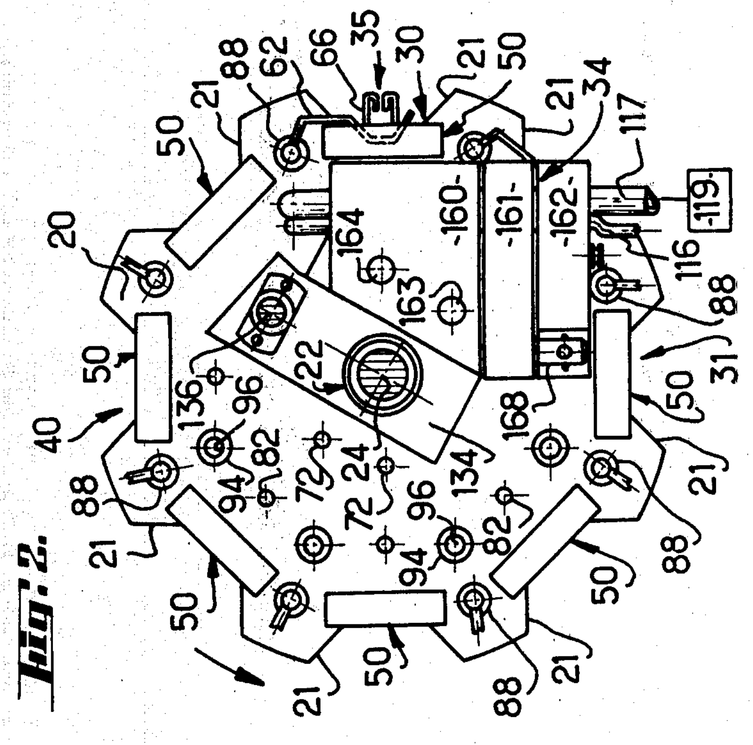
FIG. 2 is a top view of the rotative table.

The apparatus further comprises in the preferred embodiment a debeaking assembly 34 at the debeaking station 35 at the vicinity of the turntable 20, movable between an operative position and a non-operative position so that each support 30 is able to pass, upon rotation of the table 20 in the debeaking assembly station 35. It also comprises an unloading station 40 (see FIGS. 2, 4 and 5).

The invention apparatus also comprises in the preferred embodiment actuator means 41 for actuating the debeaking assembly 34, comprising a debeaking element 110, to its operative position upon arrival of a support 30 at the debeaking assembly station 35 and thereafter returning the debeaking assembly 34 to its non-operative position (shown in FIG. 1).

Suspending means 32 of each support 30 (FIG. 6) comprises a front piece 50 constituting at least the part of a headpiece, fixed at said table 20, and consisting of a metal block with a recess 54 for receiving at least a part of a bird's head. The front piece also has an opening 56 at the apex of said recess 54 just large enough to admit the tip of the beak of the bird. Recess 54 is preferably conical and is shaped to receive snugly the head of the bird being treated. Headpiece 50 is removable to allow substitution of various shapes.

Each of said supports 30 further comprises a control member 62 constituted for instance by a rod located in the path of a bird being loaded into said support 30 and for this purpose it extends horizontally across recess 54, and is bent to extend into the recess. An alternative configuration for control member 62 is to extend straight across notch 21 below the front piece 50, as at 62' in FIG. 6*a*, in which case it acts against the bird's neck rather than between its beaks.

Figure 3:
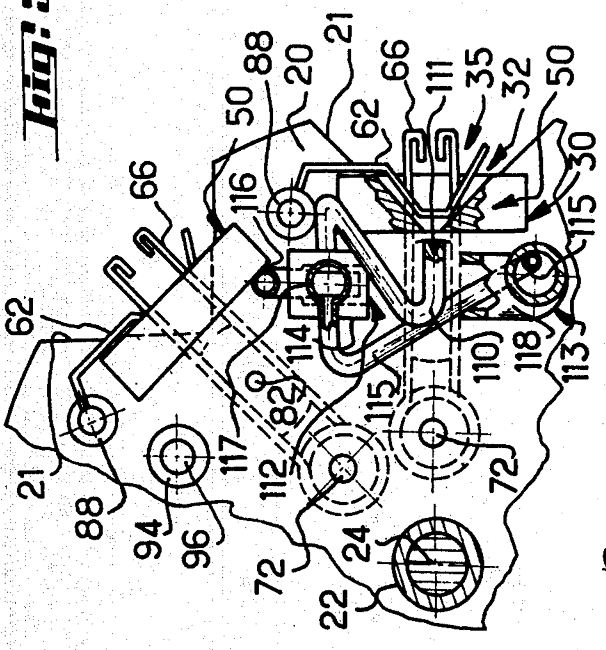
FIG. 3 is a partial top view of the rotative table showing the debeaking station.

Suspending means 32 of each support 30 also comprises a pair of retainers 66 mounted on said table 20 for holding a bird's head in said recess 54. Retainers 66 are in the shown embodiment the free ends of a coil spring 70 (FIGS. 3 to 5), and are shaped to extend across opposite sides of the bird's neck and then up along and against the back of the head. First portions 67 that cross the neck are curved to conform to the neck and to approach each other at 68, where the retainers are bent up to form vertical portions 69 curving at their free end to conform to the bird's head.

Figure 4:
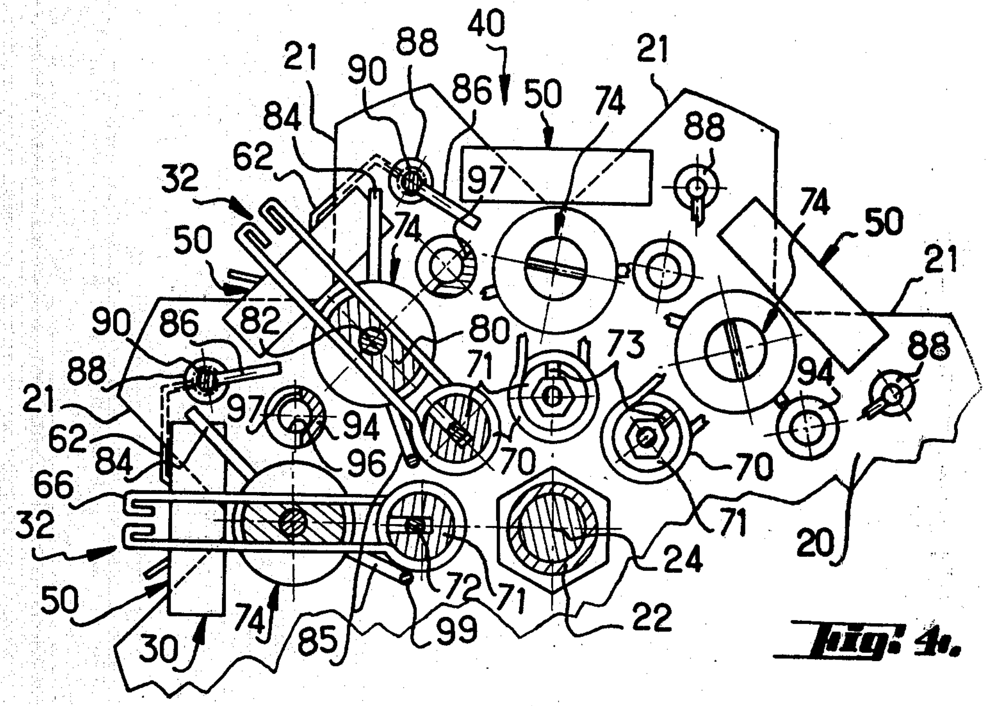
FIG. 4 is a partial underside view of the rotative table.
Figure 5:
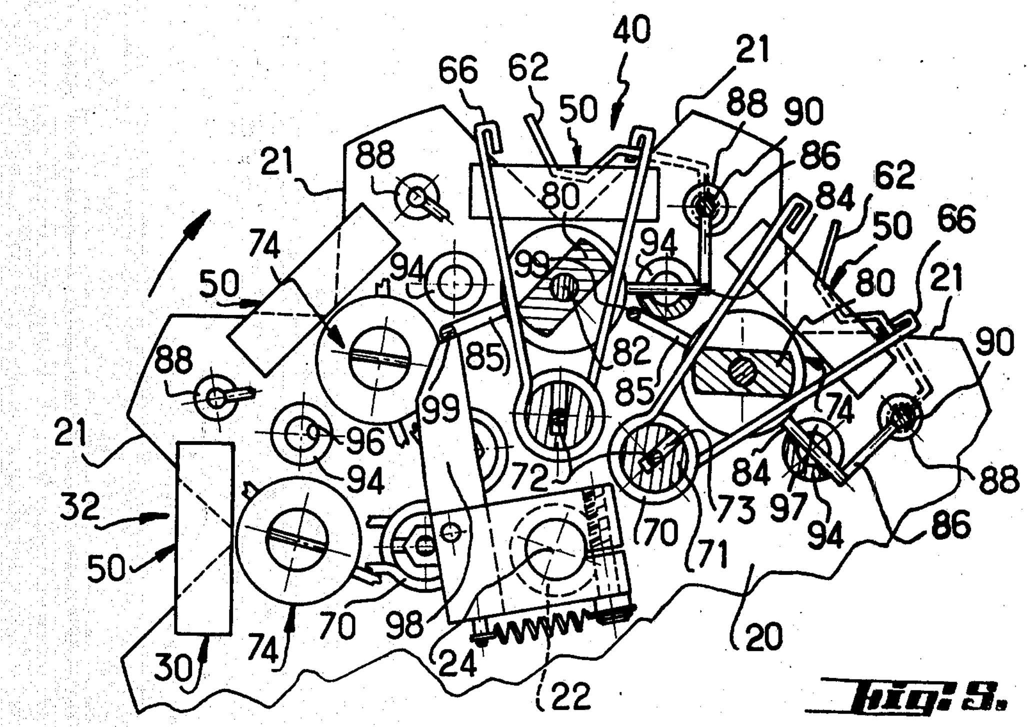
FIG. 5 is a partial underside view of the rotative table near the unloading station.
Figure 6B:
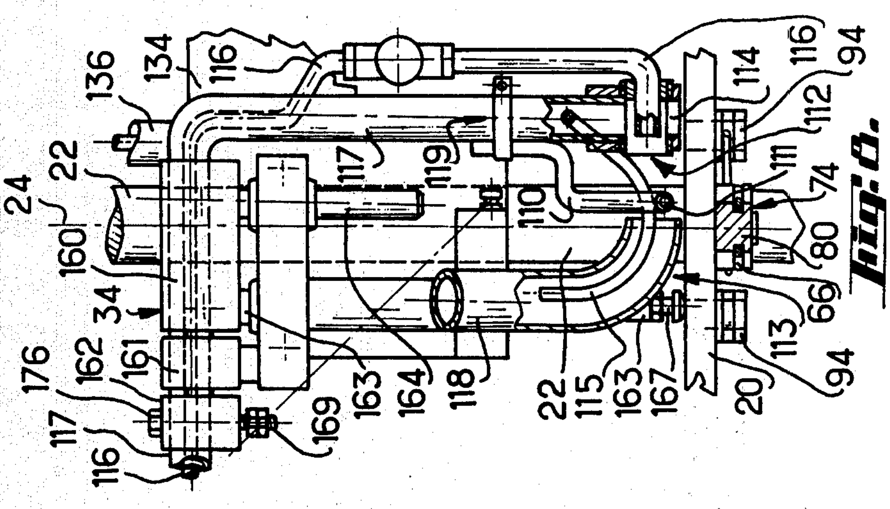
FIG. 6 is a front perspective view of a bird support of the rotative table.

Spring 70 is wrapped around disc 71, which is mounted on the under side of table 20 on post 72 which extends through slot 73 of the disc to allow adjustment radially (from axis 24) for varying the extension of retainers 66. From disc 71 retainers 66 pass between discs 76 and 78 of member 74, on opposite sides of bar-shaped eccentric cam 80 fixed between the discs. Discs 76 and 78 and cam 80 are mounted to pivot about axis 81 on shaft 82 which is fixed in table 20 for opening and closing retainers 66. To control that opening and closing, arms 84 and 85 fixed to member 74 extend in generally opposite directions from shaft 81, and arm 86 extends from post 88 to act as a stop against arm 84 (FIG. 4), preventing clockwise (from the point of view of FIG. 4, looking at the under side of table 20) rotation of cam 80, which thus holds retainers 66 open against the force of spring 70. Post 88 is mounted in table 20 to pivot about axis 89, and has fixed to it above the table an end of rod 62. When arms 84 and 86 are against each other to hold the retainers open, rod 62 is pivoted somewhat outwardly from front piece 50. A spring 90 biases post 88 in this position. Inward movement of control member 62 causes post 88 to pivot, moving arm 86 away from arm 84 to release the latter and allow spring 70 to close retainers 66, rotating cam 80 until it is aligned and balanced between the retainers (FIG. 4). To indicate whether retainers 66 are open or closed (and hence whether or not a bird is loaded between them), hollow post 94 is mounted in table 20 with its opening 96 positioned to be blocked by arm 84, which enters slot 97 of the post when the retainers are open. Post 94 thus also acts as a stop for arm 84, to protect the elastic limit of retainers 66, and acts additionally as a stop for arm 86 in its locking position (FIG. 7). Finally, for driving the release of the birds, a release element, constituted for instance by a cam 98 is mounted on the spindle 22 at unloading station 40 and is advantageously arranged in the path of downturned end 99 of arm 85, so as to pivot arm 85 and hence cam 80, counterclockwise (viewed, as before, from beneath the table 20) to the open position, whereupon spring 90 causes arm 86 to in turn pivot into place against arm 84, locking the mechanism open. It is thus clear that the above structure constitutes a linkage which, with the release element 98 form together release means for causing the support 30 to release its bird upon arrival at the unloading station 40.

Debeaking assembly 34 (FIG. 8) comprises a debeaking element 110 with an open end shaped to fit over the end of the birds beak. Although end 111 is shown in FIG. 8 with a circular cross-section, it may have other shapes, depending upon whether one or both beaks are to be burned, and upon the degree and shape of debeaking desired. This shape can be (FIGS. 16,17) conical or half-conical and so on. The debeaking assembly 34 also comprises means 112 to heat said debeaking element 110 to burn said beak. Said heating means 112 comprises a nozzle connected through tube 116 to a source of propane or other gas to provide a flame to debeaking element 110, typically to over 700° C. The debeaking assembly 34 further comprises means 113 for drawing off hot air around nozzle 114 to protect the apparatus from overheating and to remove debeaking products of combustion. Advantageously, said means 113 for drawing off air comprises an exhaust tube 118, opposite nozzle 114, which is fed with a stream of fresh air by tube 115 connected to a larger tube 117. Ventilator means 119 blows air into tube 117. Debeaking element 110 extends between nozzle 114 and exhaust tube 118 and is rigidly fixed to tube 117. It has to be noted that the free end of tube 115 is disposed at a location sufficiently spaced from said debeaking element 110 so as to avoid to cool the debeaking element 110 and above all end 111 which effects debeaking.

Drive means 27 driven by motor 26 and acting upon spindle 22 comprises as it can be seen from FIG. 10 a main shaft 120 having at one end a gear wheel 121 cooperating with and endless screw 122 on spindle 123 of pulley 124 supporting a belt 125 actuated by pulley 126 fixed onto the arm 127 of motor 26.

The other end of main shaft 120 is connected through an oldham joint 128 to a secondary shaft 129 comprising an endless screw 130 cooperating with a cog-wheel 131 fixed onto spindle 22 are rotatively mounted with the aid of several bearing blocks 132, with respect to the frame 1.

The debeaking assembly 34 is mounted onto a mobile support 134, the latter being guided near one end **134*a* by spindle 22 to freely rotate with respect to said spindle 22. The mobile support 134 bears at its lower end onto a plate 135 (see FIG. 11) which is fixed to an actuating shaft 136 forcing mobile support 134 through a hole 137 provided therethrough at a location situated preferably opposite to the end 134*a* of the mobile support 134, said actuating shaft 136 being connected to the actuator means 41** described herebelow.

Actuator means 41 comprise a wheel 140 rigidly mounted onto secondary shaft 129, constituting a double cam, each face comprising a cam path such as the cam path 141 shown in FIGS. 1, 11 and 10, the other cam path 142 being shown only on FIG. 10. In cam path 141 bears a roller 143 fixed to a lever 144 which is articulated at one end onto an axle 145 rotatively mounted onto a bearing block 146, the other end supporting a vertical rod 147 mounted articulated on said lever 144, the other end of vertical rod 147 beind connected to actuating shaft 136 through a yoke 148 passing through a port 149 provided in frame 1. A driving rod 150 is fixed onto one end of axle 145 and at the other free end supports a pushing rod 151 articulated at one end on said driving rod 150 and being articulated at the other free end to vertical rod 147. It can thus be seen that lever 144, driving rod 150, pushing rod 151 and vertical rod 147 form substantially an articulated parallelogram. Pushing rod 151 is preferably in two parts **151*a* and 151*b* which are screwed and connected with the aid of a sleeve 152 also screwed thereby varying the length of pushing rod 151 and rotation of mobile support 134**.

In the other cam path 142 is located a roller 153 fixed to one end of a lever 154 fixed at the other end to axle 145 so as to rotate axle 145 and horizontally displace pushing rod 151. Cam path 141 drives lever 144 which vertically actuates vertical rod 147 so as to ascend or lower mobile support 134 during rotation of wheel 140. Cam path 142 horizontally rotates mobile support 134.

In reference to FIG. 12, debeaking assembly 34 comprises three parts 160, 161, 162. Part 160 comprises as shown in FIG. 13 two guiding members 163, 164 passing through holes 165, 166, respectively, through mobile support 134. Guiding member 163 is long enough to abut at its free end turntable 20 when mobile support 134 is lowered, its free end being provided with a screw 167 for varying its total length. Part 161 comprises a finger 168 provided with a screw 169 interlinking part 162 to part 161. Part 162 comprises a spring hook 170 to hook a spring 171 between part 162 and hook 172 fixed on mobile support 134. Apertures 173, 174, 175 are provided respectively in parts 160,161 and 162 to leave the passage to air tube 117 and gas tube 116. However, gas tube 116 and air tube 117 are fixed to part 162 by a clamping means 176.

As shown in FIG. 14, part 161 can be interlinked with part 160 with the aid of a screw 177 able to penetrate into a hole provided in part 160.

In can also be noted that part 161 comprises at its under side a further screw 178 (shown at FIG. 13) bearing on mobile support 134 when screw 167 does not already abut turntable 20. Besides, as it can be seen from FIGS. 12 and 13, finger 168 protrudes in a recess 180 in part 160, the size of recess 180 being predetermined to allow to pivot parts 162 and 161 within determined limits when screw 177 does not engage with part 160. In such a case, since air tube 117 pivots with part 162 and debeaking element is fixed to air tube 117, this will allow debeaking element to pivot to effect debeaking. In case screw 177 engages with part 160, parts 162 and 161 are fixed to part 160 and do not pivot. In this case debeaking element 110 only lowers vertically to effect debeaking of the upper beak.

In reference to FIG. 15 is shown in more details the mechanism to lower or ascend frame 1 with respect to support base 2. This system comprises a crank 181 comprising an endless screw 182 so as to ascend or lower frame 1 with respect to support base 2. Frame 1 advantageously comprises a blocking means 183 shown on FIG. 1 to block frame 1 in a determined position.

It has to be noted that at loading station 40 can be counted the birds with the aid of any counting apparatus known per se and which has therefore not been shown in the drawings.

It has to be noted that actuator means 41 are such that debeaking assembly 34 is moved through its complete cycles the same number of times as the number of supports 30 provided on table 20 for each complete rotation of table 20.

Now it will be described the operation of the above described invention apparatus, comprising a debeaking assembly according to the above said preferred embodiment.

In operation, an operator loads a bird, such as a chick into each support 30 as it reaches station 31 by squeezing the back of the bird's head to separate its upper and lower beaks, and pressing the open beak against control member 62 to close retainers 66, as described above, and force (with the help of the conical surface of recess 54) the beak to close and go through front piece hole 56.

As table 20 rotates and a loaded bird approaches debeaking station 35, mobile support 134 is caused by actuator means 41 previously described to descend towards table 20 and causing thereby debeaking assembly 34 to also descend and pivot outwardly towards support 30. When guiding member 163 abuts against table 20, the downward motion of part 160 of the debeaking assembly ceases. However, when screw 177 does not engage part 160, continued downward motion of mobile support 134 causes parts 162 and 161 to pivot downwardly under effect of spring 171, this causing air tube 117 and gas tube 116 to pivot thereby also pivoting horizontally debeaking element 110 of a predetermined rotation until it receives and presses against the tip of the bird's beak protruding through hole 56. Throughout operation, the positive air flow from tube 115 into exhaust tube 118 induces air flow near front piece 50, into tube 118, removing excess hot air to avoid overheating the bird or the parts it touches, cooling front piece 50, and also removing products of combustion when the beak is burned.

If it is desired to effect only the debeaking of the upper beak of the bird, screw 177 is engaged into part 160 to interlink parts 162 and 161 with part 160. Thus, a downward motion of part 160 caused by downward motion of mobile support 134 will only provide a vertical downward motion of debeaking element 110 onto the upper beak to be debeaked by burning according to the present invention.

Upon completion of the debeaking, after a determined period of time provided by the cam paths of wheel 140 of actuator means 41, mobile support 134 begins to ascend, and begins to rotate parts 161 and 162 by acting upon screw 178 when screw 177 is not engaged with part 160 so that debeaking element 110 is withdrawn horizontally from the bird, and a further upward motion of mobile support 134 also causes an upward motion of debeaking assembly, the latter moving rapidly upwardly to its starting position.

At unloading station 40 birds are automatically released and counted, as already described.

Overall operation is simple and fulproof, and permits highly controlled treatment at extremely high speed, for instance, as fast as 6000 birds, such as chicks, per hour.

Of course, the present invention is by no means limited to the forms of embodiment described and illustrated, which have been given by way of example only. In particular, it comprises all the means constituting technical equivalents to the means described as well as their combinations should the latter be performed according to its spirit and carried out within the scope of the following claims. In this connection, it must be noted that the invention method and apparatus can be also applied to animals in addition to the birds which have been cited only as preferred embodiment.

What is claimed is:

1. A method of automatically debeaking birds, comprising:

providing a plurality of spaced apart bird supports, each of said bird supports comprising means for holding said bird with the head immobilized, moving said bird supports so that each of said bird supports follows a path successively passing through a bird loading station and a bird unloading station, inserting a bird into said bird support in said bird loading station, releasing said bird from said bird support in said bird unloading station, disposing a debeaking assembly at a debeaking station along said path of said bird supports downstream with respect to said loading station but upstream with respect to said unloading station, said debeaking assembly comprising a debeaking element, movable between an operative position and a non-operative position, so that each support passes through said debeaking station, and moving the debeaking assembly to its operative position upon arrival of a support at said debeaking station and thereafter returning said debeaking assembly to its non-operative position after a predetermined period of time sufficient to realize the debeaking operation.

2. The method of claim 1, wherein the period of time for debeaking is predetermined to be lower than the time of passage in regard of the debeaking assembly of two successive supports thereby allowing the debeaking assembly with its debeaking element to successively debeak each bird onto each support.

3. The method of claim 1, comprising:

moving said supports continuously in rotation at a predetermined substantially constant speed, said path comprising a closed loop, moving in rotation the debeaking assembly, at the same rotation speed as said bird supports, during the period of time where the debeaking assembly with its debeaking element is in its operative position so that the debeaking assembly follows in rotation the support with the bird in the debeaking operation, thereby providing a proper debeaking, moving the debeaking assembly in rotation in a contrary direction with respect to said bird supports rotation direction when the debeaking assembly is returned in its retracted non-operative position so as to return the debeaking assembly in its original position before debeaking.

4. The method of claim 3, comprising lowering the debeaking assembly from its non-operative position located above said bird supports, at the same time the debeaking assembly is rotated to follow said bird supports rotation and rotating horizontally with respect to the debeaking assembly, the debeaking element towards the facing support so as to debeak the facing bird.

5. The method of claim 3, comprising lowering the debeaking assembly from its non-operative position located above said bird supports, at the same time the debeaking assembly is rotated to follow said bird supports rotation and only vertically lowering with the debeaking assembly the debeaking element so as to debeak only the upper beak.

6. Apparatus for automatically supporting and restraining notably birds, comprising:

a plurality of spaced apart bird supports, each of said bird supports comprising means for grasping the head of a bird to suspend said bird with its body hanging below its head and with the head immobilized, each said support having a closed position for grasping said head and an open position in which said head is free to be inserted into or dropped from said support means, drive means for moving said bird support to cause each support to pass first to a loading station and thereafter to an unloading station, and release means at said unloading station to automatically shift said grasping means from said closed position to said open position to cause a bird to be automatically released.

7. The apparatus of claim 6, wherein said suspending means comprises a front piece constituting at least a part of a headpiece, fixed to said table and having a recess for receiving at least a part of a bird's head.

8. The apparatus of claim 7, wherein said recess is conical.

9. The apparatus according to claim 7, wherein the front piece has an opening at the apex of said recess just large enough to admit the tip of the beak of the bird.

10. The apparatus of claim 7, wherein said suspending means further comprises a pair of retainers for holding a bird's head in said recess.

11. The apparatus of claim 10, wherein each retainer is shaped to provide a first portion extending across the neck of the bird in its support, and a second portion extending along the bird's head.

12. The apparatus of claim 6, wherein said release means comprises a release element for automatically forcing said suspending means to release a bird upon arrival of said support at an unloading station.

13. The apparatus of claim 12, wherein said suspending means comprises a spring for biasing said retainers in a close position against a bird and said release means comprises a cam for forcing said retainers apart to an open position to release said bird.

14. The apparatus of claim 13, wherein each said support further comprises a control member in the path of a bird being loaded into said support for actuation of said cam with the aid of a linkage so as to allow said spring to close the retainers upon a bird when the bird is pressed against the control member.

15. The apparatus of claim 14, wherein said release element is arranged in the path of said linkage to return said cam to its position holding said retainers apart.

16. Apparatus for automatically debeaking birds, comprising:

a plurality of spaced apart bird supports, each bird support comprising means for holding a bird by its head with the head immobilized, drive means for moving said bird supports to cause each support to follow a path passing first to a loading station and thereafter to an unloading station, release means for causing a support to release its bird upon arrival at said unloading station, a debeaking assembly at a debeaking station along said path of said bird supports downstream with respect to the loading station but upstream with respect to the unloading station, said debeaking assembly comprising a debeaking element, movable between an operative position and a non-operative position so that each support is able to pass through said debeaking station, and, actuator means for actuating said debeaking assembly with its debeaking element to its operative position upon arrival of a support at the debeaking station and thereafter returning the debeaking assembly with its debeaking element to its non-operative position.

17. The apparatus of claim 16, wherein said actuator means comprises means for holding said heated debeaking element against a beak with sufficient pressure to char said beak without damaging it so as to avoid to wound or injure said beak thereby allowing the bird to feed itself.

18. The apparatus of claim 17, wherein said actuator means further comprises means for moving horizontally and debeaking element, with respect to the debeaking assembly, towards the facing support so as to debeak the facing bird.

19. The apparatus of claim 16, wherein the debeaking assembly comprises means to heat said debeaking element to burn said beak.

20. The apparatus of claim 19, wherein the debeaking end of debeaking element is open and shaped to fit over the end of the bird's beak, said shape being substantially conical.

21. The apparatus of claim 19, wherein the debeaking end of debeaking element is open and shaped to fit over the end of the bird's beak, said shape being substantially half-conical.

22. The apparatus of claim 19, wherein said heating means comprises a gas nozzle and a source of flammable gas.

23. The apparatus of claim 22, further comprising means for drawing off hot air around said nozzle to protect said apparatus for overheating and to remove debeaking products of combustion.

24. The apparatus of claim 23, wherein said means for drawing off air comprises an exhaust tube opposite said nozzle and means for blowing air into said tube at a location sufficiently spaced from said debeaking element so as to avoid to cool the debeaking element.

25. The apparatus of claim 6 or 16 wherein said bird supports are mounted on a rotatable table.

26. Apparatus for automatically debeaking birds comprising:

a bird support comprising a headpiece with a central opening, and retainer assembly for immobilizing a bird's head with its beak exposed through said opening, a debeaking element movable from a retracted position to an operative position, and means for moving said debeaking element to its operative position when a bird is held in said bird support and to its retracted position when said bird is released.

27. The apparatus of claim 26, wherein said headpiece has a conical recess surrounding said opening.

28. The apparatus of claim 26, wherein said retainer assembly comprises a pair of shaped retainers arranged to extend across opposite sides of a bird's neck and up along its head.

29. The apparatus of claim 26, wherein said bird support is movable toward and away from said debeaking element, and debeaking means comprises actuator means for actuating said debeaking element to its operative position upon arrival of said bird support at said debeaking element.

30. The apparatus of claim 26, wherein said debeaking means comprises release means for automatically releasing a bird from said bird support after debeaking.

31. The apparatus of claim 26 wherein said debeaking element comprises a debeaking end which is opened and shaped to fit over the end of the bird's beak, said shape being substantially conical.

32. The apparatus of claim 2 wherein said debeaking element comprises a debeaking end which is open and shaped to fit over the end of the bird's beak, said shape being substantially half conical.

33. A method for automatically supporting and restraining notably birds, comprising:

providing a plurality of spaced apart bird supports, each bird support comprising means for holding a bird by its head with the head immobilized, moving said bird supports so that each of said supports follows a path successively passing through a bird loading station and a bird unloading station, inserting a bird into a said bird support in said bird loading station, and releasing said bird from said bird support in said bird unloading station, wherein the bird support comprises means for grasping the head of a bird to suspend said bird with its body hanging below its head and with the head immobilized, each said support having a closed position for grasping said head and an open position in which said head is free to be inserted into or dropped from said support means, said release means at said unloading station automatically shifting said grasping means from said closed position to said open position to cause the bird to be automatically released.

34. Apparatus for automatically supporting and restraining notably birds, comprising:

a plurality of spaced apart bird supports, each bird support comprising means for holding a bird by its head with the head immobilized, each said support having a closed position for grasping said head and an open position in which said head is free to be inserted into or dropped from said support means, and wherein said bird support comprises a head piece with a central opening, and a retainer assembly for immobilizing a bird's head with its beak exposed through said opening.

35. The apparatus of claim 34, wherein said retainer assembly comprises a pair of shaped retainers arranged to extend across opposite sides of a bird's neck and up along its head.

36. The apparatus of claim 34 wherein said bird supports comprise means for grasping the head of a bird to suspend said bird with its body hanging below its head and with the head immobilized.

* * * * *